United States Patent [19]

Lewis et al.

[11] Patent Number: 4,952,244

[45] Date of Patent: Aug. 28, 1990

[54] PROTECTIVE COATINGS FOR POLYACETYLENIC RECORDING MEDIA

[75] Inventors: David F. Lewis, Monroe, Conn.; Robert D. Schenfele, Caldwell; Thomas Winkler, Maywood, both of N.J.

[73] Assignee: GAF Chemicals Corporation, Wayne, N.J.

[21] Appl. No.: 258,523

[22] Filed: Oct. 17, 1988

[51] Int. Cl.$^5$ .................... C09J 189/00; G03C 1/72
[52] U.S. Cl. .................................. 106/135; 430/270; 430/337; 430/340; 430/495
[58] Field of Search .............. 430/523, 539, 346, 340, 430/495, 270, 337; 106/135

[56] References Cited

U.S. PATENT DOCUMENTS

| | | | |
|---|---|---|---|
| 2,461,475 | 2/1949 | Kaszuba | 106/135 |
| 2,905,561 | 9/1959 | Barnett et al. | 426/125 |
| 3,501,308 | 3/1970 | Adelman | 430/337 |
| 4,581,315 | 8/1986 | Garito | 430/269 |
| 4,734,355 | 3/1988 | Lewis et al. | 430/270 |

*Primary Examiner*—Theodore Morris
*Attorney, Agent, or Firm*—Marilyn J. Maue; Joshua J. Ward

[57] ABSTRACT

The invention relates to a light stabilizing and antioxidant coating for polyacetylenic recording media which comprises an aqueous composition of ascorbic acid, gelatin and less than 2% by weight of surfactant wherein the mole ratio of acid to gelatin is between about 1:1 and about 10:1 dissolved in from about 35 wt. % to about 80 wt. % of water.

5 Claims, No Drawings

PROTECTIVE COATINGS FOR POLYACETYLENIC RECORDING MEDIA

In one aspect the invention relates to a novel coating composition to improve light stabilization and resistance to oxidation of polyacetylenic imageable film layers in a recording medium.

In another aspect, the invention relates to the method of preparing a coating composition having the above properties and in still another aspect the intention relates to the use of said coating composition.

BACKGROUND OF THE INVENTION

Several types of polyacetylenic recording media have been developed which upon exposure to a pattern transmitted by radiant energy, record information in a high degree of resolution and clarity. However, exposure of these films to UV light over extended periods, before or after imaging, resulted in development of background density such that the high degree of resolution and clarity is gradually diminished in the finished record.

Accordingly, it is an object of the present invention to overcome the above deficiency by a convenient and commercially feasible process with a relatively inexpensive composition.

Another object of this invention is to decrease inadvertent background development of exposed films and to prevent unwanted development of films before imaging when accidentally exposed to UV light.

Still another object is to prevent oxidation in imageable polyacetylenic film layers of a recording media.

These and other objects of the invention will become apparent from the following description and disclosure.

THE INVENTION

In accordance with this invention there is provided a light stabilizing and antioxidizing aqueous composition suitable for coating over an imageable polyacetylenic surface layer of a recording media, which composition comprises a solution of ascorbic acid and a crystalline polyacetylenic binder material in a mole ratio of between about 1:1 and about 10:1, preferably between about 4:1 and about 6:1, combined with a small amount, between about 0.01 and about 1 wt. % of a surfactant. The present compositions are aqueous solutions containing between about 30% and about 90% by weight of water, preferably from 50 to 80% by weight of water.

The above compositions are coated on the surface of a polyacetylenic film layer in a thickness of between about 0.25 and about 15 micrometers, preferably in a thickness between about 1 and about 8 micrometers, at a temperature of from about 30° C. about 60° C. For optimum performance, it will be observed that the coat thickness can vary inversely with the concentration of ascorbic acid in the composition.

Suitable wetting agents employed in the composition are non-ionic surfactants which include ammonium or alkali metal salts of alkoxylated sulfates or alkoxylated sulfated $C_8$ to $C_{12}$ alkyl phenols, for example, sulfamic acid ammonium salt, e.g. ALIPAL®; CD-128, CO-433, CO-436, EP-110 and sulfamic acid ammonium salts of polyglycidol based surfactants.

Binder materials which are employed in the present composition are those used for fixing crystals of imageable polyacetylenic compounds in the imaginq layer of a recording medium. Such binders include gelatin, mixtures of vinyl ether/maleic anhydride copolymer with hydroxylated benzophenone, as described in U.S. Pat. No. 4,684,688, dextran, hydrophilic cellulose ethers and esters, polyvinyl lactams, paraffin, methacrylic esters and amides and any of those named in copending U.S. Pat. application Serial No. 941,885 now U.S. Pat. No. 4,734,355; filed Dec. 15, 1986; entitled "Improving Sensitivity of Processless Recording Media" now U.S. Pat. No. 4,734,355 and in U.S. Pat. Nos. 4,066,676; 4,581,315; 3,501,308 etc. incorporated herein by reference. Of these binder materials, gelatin is most preferred.

The polyacetylenic compounds employed in the imageable layer over which the present composition is coated include any of the imageable polyacetylenic diynoic, triynoic and tetraynoic acids, their amine salts or other imageable acetylenic derivatives such as those disclosed in U.S. Pat. Nos. 4,066,676; 4,581,315; 3,501,308; 3,501,297 and 3,501,302 and in copending U.S. Pat. application Serial No. 941,885, all incorporated herein by reference.

In general the compositions of the present invention are prepared by mixing the binder particles and water at ambient temperature until the gelatinous material swells, usually within a period of from about 10 to about 60 minutes, preferably from about 25 to 40 minutes. The resulting liquid mixture is then heated to a temperature of between about 40° C. and about 75° C., preferably between about 45° C. and about 55° C., to dissolve the binder particles, after which ascorbic acid and surfactant are added with stirring until a homogeneous liquid is obtained. This material can be used directly or refrigerated and stored until ready for use.

Having thus generally described the invention, reference is now had to the accompanying examples which illustrate preferred embodiments and comparisons of coated and uncoated film; however these examples are not to be construed as limiting to the scope of the invention as more broadly set forth above and in the appended claims.

EXAMPLES 1–12

Coating compositions of the present invention were prepared as follows. Into a glass 1 liter beaker containing 47 parts by weight of water at about room temperature was introduced an amount of gelatin particles. The particles were gently stirred and allowed to swell. The resulting mixture was then heated with continued stirring to melt the gelatin particles, after which an amount of ascorbic acid and surfactant was added and stirred until a homogeneous liquid was obtained. The amounts of components in the liquid coating composition and the temperature of heating were recorded and are reported in following Table I.

TABLE I

| EXAMPLE | GELATIN gms | ASCORBIC ACID g. | SURFACTANT F-225* ml | THICKNER micrometers (nm) | SPECTRUM | EXPOSED Coated | Uncoated |
|---|---|---|---|---|---|---|---|
| 1 | 3.0 | 5.0 | .5 | 7.5 | full spectrum | 0.32 | 3.21 |
| 2 | 2.5 | 5.0 | .5 | 8.5 | full spectrum | 0.31 | 3.47 |
| 3 | 2.0 | 5.0 | .5 | 7.5 | full spectrum | 0.37 | 3.23 |
| 4 | 1.5 | 5.0 | .5 | 3.5 | full spectrum | 0.29 | 3.46 |

TABLE I-continued

| EXAMPLE | GELATIN gms | ASCORBIC ACID g. | SURFACTANT F-225* ml | THICKNER micrometers (nm) | SPECTRUM | EXPOSED Coated | EXPOSED Uncoated |
|---|---|---|---|---|---|---|---|
| 5 | 1.8 | 10.8 | .5 | 7.5 | full spectrum | 0.32 | 3.45 |
| 6 | 1.5 | 6.0 | .5 | 8.0 | full spectrum | 0.33 | 3.71 |
| 7 | 1.5 | 6.0 | .5 | 1.0 | 254 nm | 0.38 | 1.19 |
| 8 | 3.0 | 6.0 | .5 | 1.1 | 254 nm | 0.34 | 1.19 |
| 9 | 2.0 | 6.0 | .5 | 6.16 | 254 nm | 0.07 | 1.19 |
| 10 | 1.5 | 6.0 | .5 | 1.0 | 313 nm | 0.14 | 0.32 |
| 11 | 2.5 | 6.0 | .5 | 1.3 | 313 nm | 0.11 | 0.32 |
| 12 | 3.0 | 6.0 | .5 | 1.1 | 313 nm | 0.12 | 0.32 |

All Used Constant Amount of Water 47 ml
*nonyl phenol polyglycidol sulfamic acid ammonia salt

EXAMPLE 13

One half of an electron beam recording media, i.e. a supported 1-10 micrometer layer of pentacosadiynoic acid, was coated to a wet thickness of 0.003 inch with the composition of Example 1. The remaining half portion was left uncoated.

The electron recording media comprising a was exposed to the full spectrum of a Hg arc lamp at a 30 cm distance from the source. The lamp was operating at 60 V and 3.8 amp, yielding a stable light source. The spectral output for a 200 W Hg arc lamp was employed. After 5 minutes the exposure was discontinued and optical densities of the coated and uncoated portions of the film compared. The optical density of the coated portion was measured at 0.33 and that of the uncoated portion was measured at 3.71. Notwithstanding the high resistance to UV exposure, no appreciable decrease in electron beam sensitivity of the coated film resulted from the present coating.

EXAMPLE 14

The coating technique, composition and exposure of Example 9 were repeated, except that the full spectrum was reduced to a narrow band spectrum using 254 nm filter causing a lower intensity of the incident beam. The resulting optical density of the film was found to be 0.07 for the coated portion and 1.91 for the uncoated portion.

EXAMPLE 15

The coating technique, composition and exposure of Example 9 were repeated, except that the full spectrum was reduced to a narrow band at 313 nm. The coated portion of the film was found to have an optical density of 0.10, whereas the uncoated portion had an optical density of 0.32.

From the above examples it was found that film overcoated with an aqueous solution of gelatin, ascorbic acid and surfactant had greatly increased stability towards exposure of the full spectrum of a 200 W Hg arc lamp at 30 cm. The amount of stability provided depends on the gelatin layer thickness and the concentration of ascorbic acid in the coating layer. The ascorbic acid containing layer has additional beneficial properties in that it is nontoxic and protects the medium from abrasion. Also, it is compatible with the formulation in high concentrations without causing uncontrollable crystallization on standing. Preferred formulations contain a substantial excess of ascorbic acid so as to achieve maximum protection with a minimum thickness of coating.

Many modifications and alterations in the present coating compositions will become apparent to those skilled in the art from the above description and disclosure. For example, other binder materials can be substituted for gelatin in the above examples to give beneficial resistance to oxidation and light stabilization of recording media. It will also become apparent that thinner or thicker films of the coating material can be applied to the polyacetylenic underlayer to meet the needs of different UV exposure intensities.

Having thus described the invention, what is claimed is:

1. A composition comprising imageable polyacetylenic crystals in a fixing medium coated with an aqueous solution of ascorbic acid and a binder compatible with said polyacetylenic crystals in said medium; said aqueous solution having a mole ratio of ascorbic acid to binder of between about 4:1 and about 10:1 and containing from about 0.1 to about 1 wt. % of a non-ionic surfactant.

2. The composition of claim 1 wherein the mole ratio of ascorbic acid to binder is between about 4:1 and about 6:1.

3. The composition of claim 1 wherein said binder is gelatin.

4. The composition of claim 1 wherein the surfactant is nonyl phenol polyglycidol sulfamic acid ammonium salt.

5. The composition of claim 1 wherein the components are dissolved in between about 50% and about 80% by weight of water.

* * * * *